(12) United States Patent
Grammenos et al.

(10) Patent No.: US 6,482,984 B2
(45) Date of Patent: Nov. 19, 2002

(54) IMINOOXY-SUBSTITUTED BENZYL PHENYL ETHERS, PROCESSES AND INTERMEDIATES FOR THEIR PREPARATION, COMPOSITIONS COMPRISING THEM, AND THEIR USE FOR CONTROLLING HARMFUL FUNGI

(75) Inventors: Wassilios Grammenos, Ludwigshafen (DE); Hubert Sauter, Mannheim (DE); Andreas Gypser, Mannheim (DE); Markus Gewehr, Kastellaun (DE); Jordi Tormo i Blasco, Limburgerhof (DE); Arne Ptock, Ludwigshafen (DE); Bernd Müller, Frankenthal (DE); Oliver Cullmann, Mannheim (DE); Thomas Grote, Wachenheim (DE); Eberhard Ammermann, Heppenheim (DE); Siegfried Strathmann, Limburgerhof (DE); Gisela Lorenz, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/760,710

(22) Filed: Jan. 17, 2001

(65) Prior Publication Data
US 2002/0082303 A1 Jun. 27, 2002

(30) Foreign Application Priority Data
Jan. 21, 2000 (DE) .......................... 100 02 661

(51) Int. Cl.$^7$ .................... C07C 233/05; C07C 229/06; A01N 37/18
(52) U.S. Cl. .................. 564/164; 564/165; 560/35; 514/539; 514/620
(58) Field of Search ............. 560/35; 564/164, 564/165; 514/539, 620

(56) References Cited
U.S. PATENT DOCUMENTS

| 4,829,085 A | 5/1989 | Wenderoth |
| 4,937,372 A | 6/1990 | Wenderoth |
| 5,166,399 A | 11/1992 | Schuetz |
| 5,298,527 A | 3/1994 | Grammenos |
| 5,358,968 A | 10/1994 | Oberdorf |
| 5,395,854 A | 3/1995 | Brand |

FOREIGN PATENT DOCUMENTS

| EP | 253 213 | 1/1988 |
| EP | 280 185 | 8/1988 |
| EP | 386 561 | 9/1990 |
| EP | 477 631 | 4/1992 |
| EP | 513 580 | 11/1992 |
| EP | 579 124 | 1/1994 |

Primary Examiner—Shailendra Kumar
(74) Attorney, Agent, or Firm—Keil & Weinkauf

(57) ABSTRACT

Iminooxy-substituted benzyl phenyl ethers of the formula I

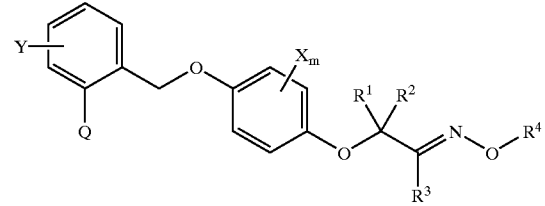

in which the substituents and the index are as defined below:

Y is H, $CH_3$, F or Cl;
Q is $C(=CHOCH_3)$—$COOCH_3$, $C(=CHCH_3)$—$COOCH_3$, $C(=NOCH_3)$—$COOCH_3$, $C(=NOCH_3)$—$CONHCH_3$ or $N(-OCH_3)$—$COOCH_3$;
X is hydrogen, halogen, alkyl, alkoxy or $CF_3$;
m is 1 or 2, where the radicals X may be different if m=2;
$R^1$ is alkyl and
$R^2$ is hydrogen or alkyl; or
$R^1$ and $R^2$ together are cyclopropyl, cyclopentyl or cyclohexyl;
$R^3$ is alkyl or $CF_3$; and
$R^4$ is alkyl, alkenyl, alkynyl, haloalkyl, haloalkenyl or haloalkynyl;

processes and intermediates for their preparation, compositions comprising them, and their use, are described.

9 Claims, No Drawings

IMINOOXY-SUBSTITUTED BENZYL PHENYL ETHERS, PROCESSES AND INTERMEDIATES FOR THEIR PREPARATION, COMPOSITIONS COMPRISING THEM, AND THEIR USE FOR CONTROLLING HARMFUL FUNGI

The present invention relates to iminooxy-substituted benzyl phenyl ethers of the formula I

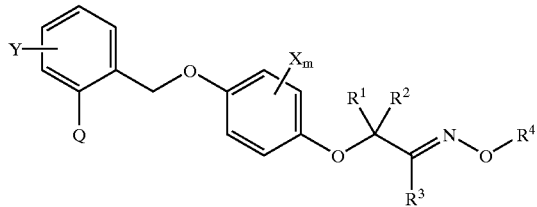

in which the substituents and the index have the following meanings:

Y is H, $CH_3$, F or Cl;
Q is $C(=CHOCH_3)$—$COOCH_3$, $C(=CHCH_3)$—$COOCH_3$, $C(=NOCH_3)$—$COOCH_3$, $C(=NOCH_3)$—$CONHCH_3$ or $N(-OCH_3)$—$COOCH_3$;
X is hydrogen, halogen, $C_1$–$C_4$-alkyl, $C_1$–$C_4$-alkoxy or $CF_3$;
m is 1 or 2, where the radicals x may be different if m=2;
$R^1$ is $C_1$–$C_4$-alkyl and
$R^2$ is hydrogen or $C_1$–$C_4$-alkyl; or
$R^1$ and $R^2$ together are cyclopropyl, cyclopentyl or cyclohexyl;
$R^3$ is $C_1$–$C_6$-alkyl or $CF_3$; and
$R^4$ is $C_1$–$C_4$-alkyl, $C_3$–$C_4$-alkenyl, $C_3$–$C_4$-alkynyl, $C_1$–$C_4$-haloalkyl, $C_3$–$C_4$-haloalkenyl or $C_3$–$C_4$-haloalkynyl;
and their salts.

In addition, the invention relates to processes and intermediates for preparing the compounds I, and also to compositions, and to the use of the compounds I for controlling harmful fungi.

Phenylcarbamates having a phenoxymethylene group in the ortho position are disclosed in WO-A 93/15046. α-phenylacrylic acid and α-phenyl-α-methoximinoacetic acid derivatives having a phenoxymethylene grouping in the ortho position are known from EP-A 253 213, EP-A 280 185, EP-A 386 561, EP-A 477 631, EP-A 513 580 and EP-A 579 124. Some of the compounds described in these publications carry an oximino radical on the phenoxy grouping.

The compounds described in the abovementioned publications are suitable for use as crop protection agents against harmful fungi.

However, their action is frequently unsatisfactory. It is an object of the present invention to provide compounds having improved activity.

We have found that this object is achieved by the substituted benzyl phenyl ethers of the formula I. Furthermore, we have found intermediates and processes for preparing the compounds I, and the use of the compounds I and compositions comprising them for controlling harmful fungi.

The compounds of the formula I differ from the compounds known from the abovementioned publications in that the phenoxy group is substituted by the oximino radical, which is attached via oxygen. Compared to known compounds, the compounds of the formula I have increased activity against harmful fungi.

Compounds of the formula I are obtained, for example, starting from hydroxy compounds of the formula II

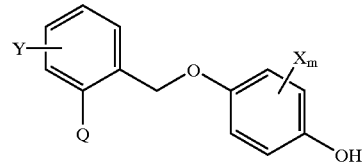

which are obtainable by oxidation of acetyl compounds of the formula II.1.

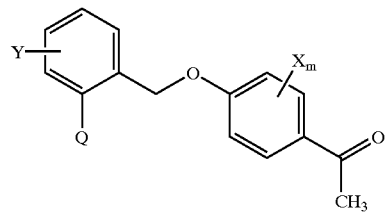

The oxidation is usually carried out at temperatures of from −20° C. to 60° C., preferably from 0° C. to 30° C., in an inert organic solvent or water in the presence of a base or a buffer, such as, for example, $Na_2HPO_4$ [cf. Synthesis, (1991), 63; Heterocycles (1993), 819; Tetrahedron (1995), 3197]. Suitable oxidizing agents are, for example, hydrogen peroxide, m-chloroperbenzoic acid, peracetic acid, $H_2O_2$ ×$BF_3$, peroxytrifluoroacetic acid or $K_2S_2O_7/H_2SO_4$.

Suitable solvents are, in general, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and suitable bases are inorganic compounds, such as alkali metal and alkaline earth metal hydroxides, such as lithium hydroxide, sodium hydroxide, potassium hydroxide and calcium hydroxide. Particular preference is given to sodium hydroxide.

In general, the base is employed in catalytic amounts; however, it can also be employed in equimolar amounts or in excess.

The oxidation of the acetyl compounds II.1 can also be carried out in two steps. Primarily, it leads to acetyloxy compounds of the formula II.2 from which, directly or, if desired, in a separate step, the hydroxy compound II can be released under basic conditions.

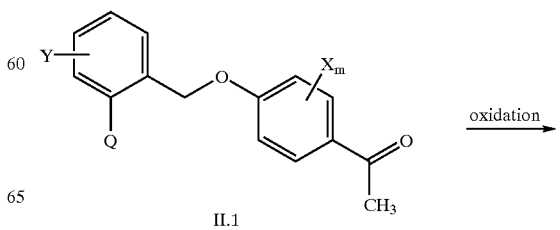

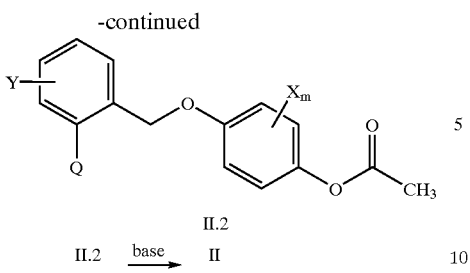

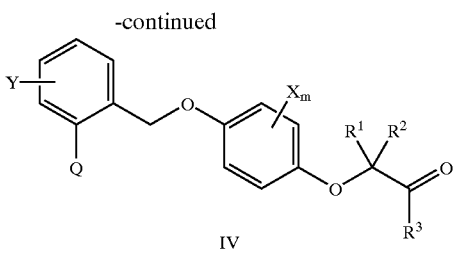

Compounds of the formula I in which Q is C(=NOCH₃)—CONHCH₃ are preferably prepared using compounds II.1 in which Q is C(=NOCH₃)—COOCH₃ as starting materials in the reaction sequence outlined above, and using methylamine as base in the second step.

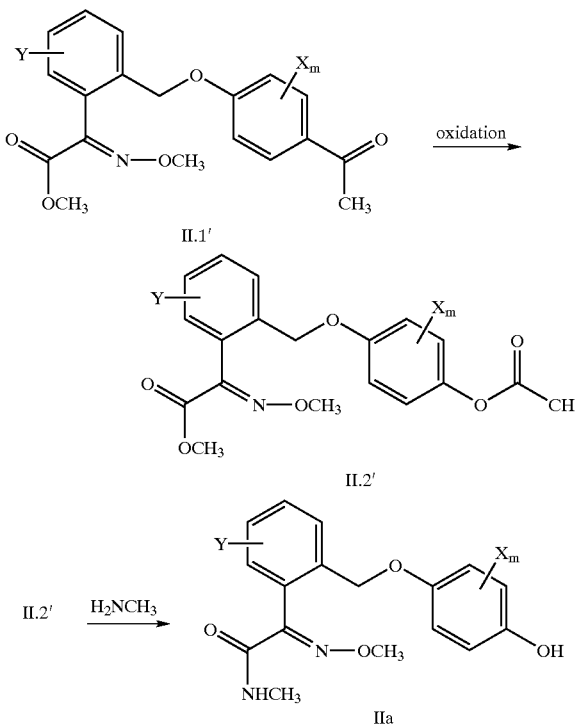

The starting materials II.1 required for the preparation of the compounds I are known from the literature [Cf. EP-A 513 580; EP-A 621 264], or they can be prepared in accordance with the quoted literature.

Hydroxy compounds of the formula II are reacted with keto compounds of the formula III to give compounds of the formula IV.

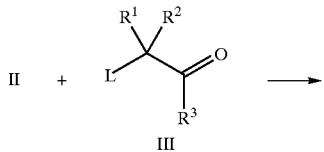

In formula III, L is a nucleophilically exchangeable group, such as halogen, preferably chlorine. The reaction is usually carried out at temperatures of from −10° C. to 120° C., preferably from 20° C. to 90° C., in an inert organic solvent in the presence of a base [cf. DE-A 38 27 222].

Suitable solvents are ethers, nitriles, ketones, such as acetone, methyl ethyl ketone, diethyl ketone and tert-butyl methyl ketone, and also dimethyl sulfoxide, dimethyl formamide and dimethyl acetamide, particularly preferably dimethyl formamide, acetone and dimethyl acetamide. It is also possible to use mixtures of the solvents mentioned.

Suitable bases are, in general, inorganic compounds, such as alkali metal and alkaline earth metal hydroxides, alkali metal and alkaline earth metal hydrides, alkali metal amides, alkali metal and alkaline earth metal carbonates, such as lithium carbonate, potassium carbonate and calcium carbonate, and also alkali metal bicarbonates, such as sodium bicarbonate, alkali metal and alkaline earth metal alkoxides, such as sodium methoxide, sodium ethoxide, potassium ethoxide, potassium tert-butoxide and dimethoxymagnesium. Particular preference is given to sodium bicarbonate, potassium carbonate, sodium methoxide and sodium hydroxide.

In general, the bases are employed in catalytic amounts; however, they can also be employed in equimolar amounts or in excess.

The starting materials are generally reacted with one another in equimolar amounts. In terms of yield, it may be advantageous to use an excess of III, based on II.

Keto compounds of the formula III are known. Some of them are commercially available, or they can be prepared by known methods [(Synthesis (1990), 595; DE-A 27 16 895; Can.J.Chem. (1972), 2387; Tetrahedron (1970), 5191; Synthesis (1977), 189–191; EP-A 297 383; EP-A 298 332; Bull.Soc.Chim.Fr. (1973), 2732; J.Org.Chem. (1995), 8320; J.Organomet.Chem. (1975), 325].

The conversion of IV into the compounds of the formula I is carried out using amino compounds V which are preferably employed as aqueous solution or in the form of their acid addition salts, for example as hydrochlorides.

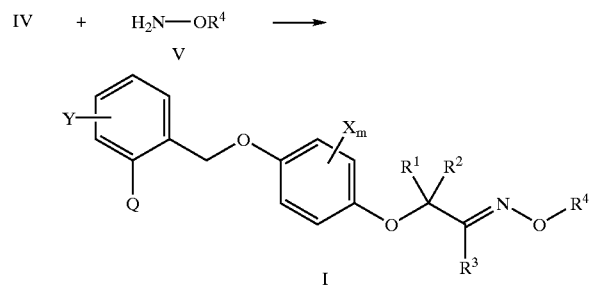

This reaction is usually carried out at temperatures of from 0° C. to 120° C., preferably from 20° C. to 80° C., in an inert organic solvent in the presence of a base [cf. EP-A 386 561].

Suitable solvents are aromatic hydrocarbons, such as toluene, or alcohols, such as methanol or ethanol, particularly preferably methanol. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal carbonates, such as lithium carbonate, potassium carbonate and calcium carbonate, and also alkali metal bicarbonates, such as sodium bicarbonate; furthermore organic bases, for example tertiary amines, such as trimethylamine, triethylamine, triisopropylamine. Particular preference is given to sodium hydroxide, potassium carbonate and triethylamine.

The bases are generally employed in catalytic amounts; however, they can also be employed in equimolar amounts, in excess or, if appropriate, as solvent.

The starting materials are generally reacted with one another in equimolar amounts. In terms of yield, it may be advantageous to employ an excess of V, based on IV.

The reaction mixtures are worked up in a customary manner, for example by mixing with water, phase separation and, if appropriate, chromatographic purification of the crude products. In some cases, the intermediates and end products are obtained in the form of colorless or pale brown viscous oils, which are purified or freed from volatile components under reduced pressure and at moderately elevated temperature. If the intermediates and end products are obtained as solids, they can also be purified by recrystallization or digestion.

In the definitions of the symbols given in the above formulae, collective terms were used which generally represent the following substituents:

Halogen: fluorine, chlorine, bromine and iodine;

Alkyl: saturated, straight-chain or branched hydrocarbon radicals having 1 to 4 or 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 4 carbon atoms (as mentioned above), where some or all of the hydrogen atoms in these groups may be replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 carbon atoms (as mentioned above) which are attached to the skeleton via an oxygen atom (—O—);

Alkenyl: unsaturated, straight-chain or branched hydrocarbon radicals having 3 or 4 carbon atoms and a double bond in any position, such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl;

Haloalkenyl: unsaturated, straight-chain or branched hydrocarbon radicals having 3 or 4 carbon atoms and a double bond in any position (as mentioned above), where some or all of the hydrogen atoms in these groups may be replaced by halogen atoms as mentioned above, in particular by fluorine, chlorine and-bromine;

Alkynyl: straight-chain or branched hydrocarbon groups having 3 or 4 carbon atoms and a triple bond in any position, such as 1-propynyl, 2-propynyl, 1-butynyl, 2-butynyl, 3-butynyl, 1-methyl-2-propynyl;

Haloalkynyl: unsaturated, straight-chain or branched hydrocarbon radicals having 3 or 4 carbon atoms and a triple bond in any position (as mentioned above), where some or all of the hydrogen atoms in these groups may be replaced by halogen atoms as mentioned above, in particular by fluorine, chlorine and bromine.

With respect to the intended use of the benzyl phenyl ethers of the formula I, particular preference is given to the following meanings of the substituents, in each case on their own or in combination:

Preference is given to compounds of the formula I in which X is located in the 2-position and is not hydrogen.

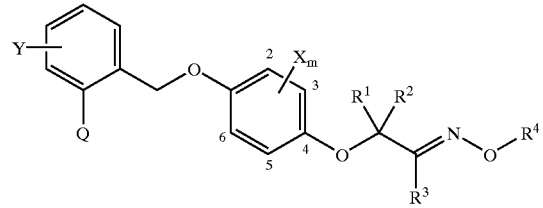

Particular preference is given to compounds of the formula Ia.

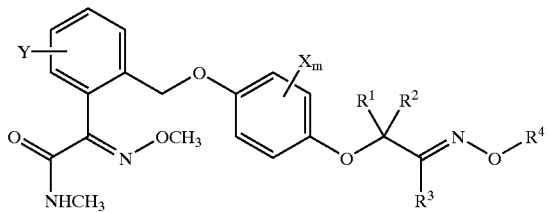

In addition, preference is also given to compounds of the formula Ib.

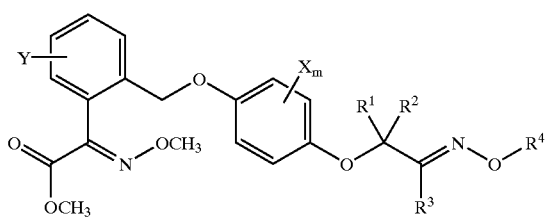

Moreover, preference is also given to compounds of the formula Ic.

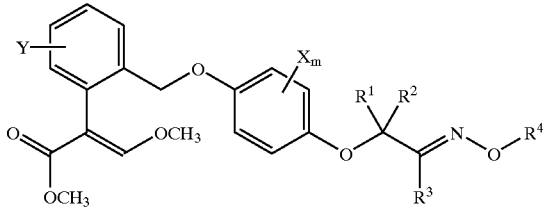

Likewise, preference is also given to compounds of the formula Id.

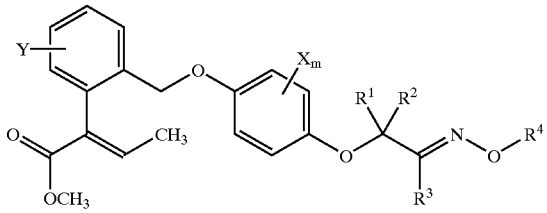

Furthermore, preference is given to compounds of the formula Ie.

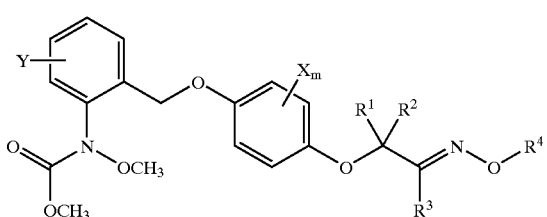

In particular, preference is given to compounds I'.

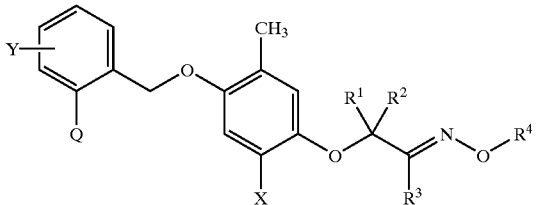

Likewise, particular preference is given to compounds I' in which X is hydrogen.

Moreover, particular preference is given to compounds I in which Q is $C(=NOCH_3)-COOCH_3$, $C(=NOCH_3)-CONHCH_3$ or $N(-OCH_3)-COOCH_3$.

Likewise, particular preference is given to compounds I' in which Y is located in the 6-position.

Moreover, particular preference is given to compounds I in which Y is hydrogen.

In addition, particular preference is given to compounds I".

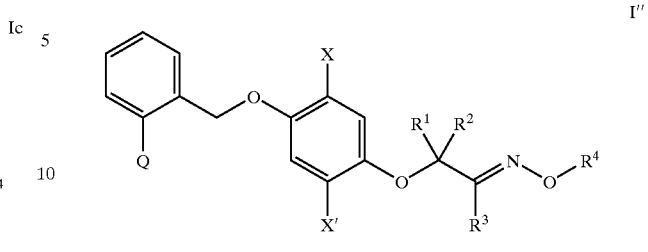

Particular preference is also given to compounds I' in which X is hydrogen, methyl or chlorine.

Moreover, particular preference is given to compounds I' in which $R^1$ is methyl, ethyl or isopropyl and $R^2$ is hydrogen.

Likewise, particular preference is given to compounds I' in which $R^1$ and $R^2$ together are dimethyl or cyclopropyl.

In addition, particular preference is given to compounds I' in which $R^3$ is methyl or ethyl.

Furthermore, particular preference is given to compounds I' in which $R^4$ is $C_1$–$C_4$-alkyl.

The particularly preferred embodiments of the intermediates with respect to the variables correspond to those of the radicals Y, Q, $X_m$, $R^1$, $R^2$, $R^3$ and $R^4$ of the formula I.

With respect to their use, particular preference is given to the compounds I compiled in the Tables below. Moreover, the groups mentioned for a substituent in the Tables are on their own, independently of the combination in which they are mentioned, a particularly preferred embodiment of the substituent in question.

Table 1
Compounds of the formula I in which Q is $C(=NOCH_3)-CONHCH_3$, $R^1$ is methyl and $R^2$ is hydrogen and the combination of the radicals Y, X, X', $R^3$ and $R^4$ for a compound corresponds in each case to a row of Table A Table 2
Compounds of the formula I in which Q is $C(=NOCH_3)-COOCH_3$, $R^1$ is methyl and $R^2$ is hydrogen and the combination of the radicals Y, X, X', $R^3$ and $R^4$ for a compound corresponds in each case to a row of Table A Table 3
Compounds of the formula I in which Q is $C(=CHOCH_3)-COOCH_3$, $R^1$ is methyl and $R^2$ is hydrogen and the combination of the radicals Y, X, X', $R^3$ and $R^4$ for a compound corresponds in each case to a row of Table A Table 4
Compounds of the formula I in which Q is $C(=CHCH_3)-COOCH_3$, $R^1$ is methyl and $R^2$ is hydrogen and the combination of the radicals Y, X, X', $R^3$ and $R^4$ for a compound corresponds in each case to a row of Table A Table 5
Compounds of the formula I in which Q is $N(-OCH_3)-COOCH_3$, $R^1$ is methyl and $R^2$ is hydrogen and the combination of the radicals Y, X, X', $R^3$ and $R^4$ for a compound corresponds in each case to a row of Table A Table 6
Compounds of the formula I in which Q is $C(=NOCH_3)-CONHCH_3$, $R^1$ is methyl and $R^2$ is methyl and the combination of the radicals Y, X, X', $R^3$ and $R^4$ for a compound corresponds in each case to a row of Table A Table 7
Compounds of the formula I in which Q is $C(=NOCH_3)-COOCH_3$, $R^1$ is methyl and $R^2$ is methyl and the combination of the radicals Y, X, X', $R^3$ and $R^4$ for a compound corresponds in each case to a row of Table A Table 8

Compounds of the formula I in which Q is $C(=CHOCH_3)$—$COOCH_3$, $R^1$ is methyl and $R^2$ is methyl and the combination of the radicals Y, X, X', $R^3$ and $R^4$ for a compound corresponds in each case to a row of Table A Table 9

Compounds of the formula I in which Q is $C(=CHCH_3)$—$COOCH_3$, $R^1$ is methyl and $R^2$ is methyl and the combination of the radicals Y, X, X', $R^3$ and $R^4$ for a compound corresponds in each case to a row of Table A Table 10

Compounds of the formula I in which Q is $N(-OCH_3)$—$COOCH_3$, $R^1$ is methyl and $R^2$ is methyl and the combination of the radicals Y, X, X', $R^3$ and $R^4$ for a compound corresponds in each case to a row of Table A Table 11

Compounds of the formula I in which Q is $C(=NOCH_3)$—$CONHCH_3$, $R^1$ is ethyl and $R^2$ is hydrogen and the combination of the radicals Y, X, X', $R^3$ and $R^4$ for a compound corresponds in each case to a row of Table A Table 12

Compounds of the formula I in which Q is $C(=NOCH_3)$—$COOCH_3$, $R^1$ is ethyl and $R^2$ is hydrogen and the combination of the radicals Y, X, X', $R^3$ and $R^4$ for a compound corresponds in each case to a row of Table A Table 13

Compounds of the formula I in which Q is $C(=CHOCH_3)$—$COOCH_3$, $R^1$ is ethyl and $R^2$ is hydrogen and the combination of the radicals Y, X, X', $R^3$ and $R^4$ for a compound corresponds in each case to a row of Table A Table 14

Compounds of the formula I in which Q is $C(=CHCH_3)$—$COOCH_3$, $R^1$ is ethyl and $R^2$ is hydrogen and the combination of the radicals Y, X, X', $R^3$ and $R^4$ for a compound corresponds in each case to a row of Table A Table 15

Compounds of the formula I in which Q is $N(-OCH_3)$—$COOCH_3$, $R^1$ is ethyl and $R^2$ is hydrogen and the combination of the radicals Y, X, X', $R^3$ and $R^4$ for a compound corresponds in each case to a row of Table A Table 16

Compounds of the formula I in which Q is $C(=NOCH_3)$—$CONHCH_3$, $R^1$ is isopropyl and $R^2$ is hydrogen and the combination of the radicals Y, X, X', $R^3$ and $R^4$ for a compound corresponds in each case to a row of Table A Table 17

Compounds of the formula I in which Q is $C(=NOCH_3)$—$COOCH_3$, $R^1$ is isopropyl and $R^2$ is hydrogen and the combination of the radicals Y, X, X', $R^3$ and $R^4$ for a compound corresponds in each case to a row of Table A Table 18

Compounds of the formula I in which Q is $C(=CHOCH_3)$—$COOCH_3$, $R^1$ is isopropyl and $R^2$ is hydrogen and the combination of the radicals Y, X, X', $R^3$ and $R^4$ for a compound corresponds in each case to a row of Table A Table 19

Compounds of the formula I in which Q is $C(=CHCH_3)$—$COOCH_3$, $R^1$ is isopropyl and $R^2$ is hydrogen and the combination of the radicals Y, X, X', $R^3$ and $R^4$ for a compound corresponds in each case to a row of Table A Table 20

Compounds of the formula I in which Q is $N(-OCH_3)$—$COOCH_3$, $R^1$ is isopropyl and $R^2$ is hydrogen and the combination of the radicals Y, X, X', $R^3$ and $R^4$ for a compound corresponds in each case to a row of Table A Table 21

Compounds of the formula I in which Q is $C(=NOCH_3)$—$CONHCH_3$, $R^1$ and $R^2$ together are cyclopropyl and the combination of the radicals Y, X, X', $R^3$ and $R^4$ for a compound corresponds in each case to a row of Table A Table 22

Compounds of the formula I in which Q is $C(=NOCH_3)$—$COOCH_3$, $R^1$ and $R^2$ together are cyclopropyl and the combination of the radicals Y, X, X', $R^3$ and $R^4$ for a compound corresponds in each case to a row of Table A Table 23

Compounds of the formula I in which Q is $C(=CHOCH_3)$—$COOCH_3$, $R^1$ and $R^2$ together are cyclopropyl and the combination of the radicals Y, X, X', $R^3$ and $R^4$ for a compound corresponds in each case to a row of Table A Table 24

Compounds of the formula I in which Q is $C(=CHCH_3)$—$COOCH_3$, $R^1$ and $R^2$ together are cyclopropyl and the combination of the radicals Y, X, X', $R^3$ and $R^4$ for a compound corresponds in each case to a row of Table A Table 25

Compounds of the formula I in which Q is $N(-OCH_3)$—$COOCH_3$, $R^1$ and $R^2$ together are cyclopropyl and the combination of the radicals Y. X, X', $R^3$ and $R^4$ for a compound corresponds in each case to a row of Table A

TABLE A

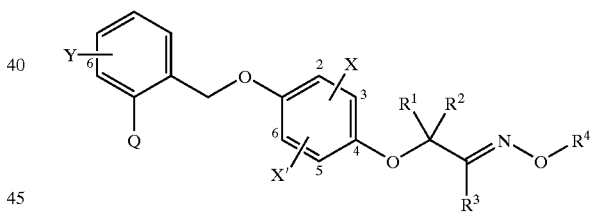

| No. | Y | X | X' | $R^3$ | $R^4$ |
|---|---|---|---|---|---|
| A-1 | H | 2-$CH_3$ | H | $CH_3$ | $CH_3$ |
| A-2 | H | 2-$CH_3$ | 5-$CH_3$ | $CH_3$ | $CH_3$ |
| A-3 | H | 2-$CH_3$ | 5-Cl | $CH_3$ | $CH_3$ |
| A-4 | H | 2-$CH_3$ | 5-F | $CH_3$ | $CH_3$ |
| A-5 | H | 2-$CH_3$ | 5-$CF_3$ | $CH_3$ | $CH_3$ |
| A-6 | 6-$CH_3$ | 2-$CH_3$ | H | $CH_3$ | $CH_3$ |
| A-7 | 6-$CH_3$ | 2-$CH_3$ | 5-$CH_3$ | $CH_3$ | $CH_3$ |
| A-8 | 6-$CH_3$ | 2-$CH_3$ | 5-Cl | $CH_3$ | $CH_3$ |
| A-9 | 6-$CH_3$ | 2-$CH_3$ | 5-F | $CH_3$ | $CH_3$ |
| A-10 | 6-$CH_3$ | 2-$CH_3$ | 5-$CF_3$ | $CH_3$ | $CH_3$ |
| A-11 | 6-Cl | 2-$CH_3$ | H | $CH_3$ | $CH_3$ |
| A-12 | 6-Cl | 2-$CH_3$ | 5-$CH_3$ | $CH_3$ | $CH_3$ |
| A-13 | 6-Cl | 2-$CH_3$ | 5-Cl | $CH_3$ | $CH_3$ |
| A-14 | 6-Cl | 2-$CH_3$ | 5-F | $CH_3$ | $CH_3$ |
| A-15 | 6-Cl | 2-$CH_3$ | 5-$CF_3$ | $CH_3$ | $CH_3$ |
| A-16 | H | 2-$CH_3$ | H | $CH_2CH_3$ | $CH_3$ |
| A-17 | H | 2-$CH_3$ | 5-$CH_3$ | $CH_2CH_3$ | $CH_3$ |
| A-18 | H | 2-$CH_3$ | 5-Cl | $CH_2CH_3$ | $CH_3$ |
| A-19 | H | 2-$CH_3$ | 5-F | $CH_2CH_3$ | $CH_3$ |
| A-20 | H | 2-$CH_3$ | 5-$CF_3$ | $CH_2CH_3$ | $CH_3$ |
| A-21 | 6-$CH_3$ | 2-$CH_3$ | H | $CH_2CH_3$ | $CH_3$ |
| A-22 | 6-$CH_3$ | 2-$CH_3$ | 5-$CH_3$ | $CH_2CH_3$ | $CH_3$ |
| A-23 | 6-$CH_3$ | 2-$CH_3$ | 5-Cl | $CH_2CH_3$ | $CH_3$ |

TABLE A-continued

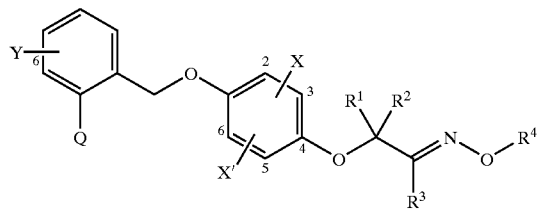

| No. | Y | X | X' | R³ | R⁴ |
|---|---|---|---|---|---|
| A-24 | 6-CH₃ | 2-CH₃ | 5-F | CH₂CH₃ | CH₃ |
| A-25 | 6-CH₃ | 2-CH₃ | 5-CF₃ | CH₂CH₃ | CH₃ |
| A-26 | 6-Cl | 2-CH₃ | H | CH₂CH₃ | CH₃ |
| A-27 | 6-Cl | 2-CH₃ | 5-CH₃ | CH₂CH₃ | CH₃ |
| A-28 | 6-Cl | 2-CH₃ | 5-Cl | CH₂CH₃ | CH₃ |
| A-29 | 6-Cl | 2-CH₃ | 5-F | CH₂CH₃ | CH₃ |
| A-30 | 6-Cl | 2-CH₃ | 5-CF₃ | CH₂CH₃ | CH₃ |
| A-31 | H | 2-CH₃ | H | CF₃ | CH₃ |
| A-32 | H | 2-CH₃ | 5-CH₃ | CF₃ | CH₃ |
| A-33 | H | 2-CH₃ | 5-Cl | CF₃ | CH₃ |
| A-34 | H | 2-CH₃ | 5-F | CF₃ | CH₃ |
| A-35 | H | 2-CH₃ | 5-CF₃ | CF₃ | CH₃ |
| A-36 | 6-CH₃ | 2-CH₃ | H | CF₃ | CH₃ |
| A-37 | 6-CH₃ | 2-CH₃ | 5-CH₃ | CF₃ | CH₃ |
| A-38 | 6-CH₃ | 2-CH₃ | 5-Cl | CF₃ | CH₃ |
| A-39 | 6-CH₃ | 2-CH₃ | 5-F | CF₃ | CH₃ |
| A-40 | 6-CH₃ | 2-CH₃ | 5-CF₃ | CF₃ | CH₃ |
| A-41 | 6-Cl | 2-CH₃ | H | CF₃ | CH₃ |
| A-42 | 6-Cl | 2-CH₃ | 5-CH₃ | CF₃ | CH₃ |
| A-43 | 6-Cl | 2-CH₃ | 5-Cl | CF₃ | CH₃ |
| A-44 | 6-Cl | 2-CH₃ | 5-F | CF₃ | CH₃ |
| A-45 | 6-Cl | 2-CH₃ | 5-CF₃ | CF₃ | CH₃ |
| A-46 | H | 3-CH₃ | H | CH₃ | CH₃ |
| A-47 | H | 3-CH₃ | 5-CH₃ | CH₃ | CH₃ |
| A-48 | H | 3-CH₃ | 5-Cl | CH₃ | CH₃ |
| A-49 | H | 3-CH₃ | 5-F | CH₃ | CH₃ |
| A-50 | H | 3-CH₃ | 5-CF₃ | CH₃ | CH₃ |
| A-51 | H | 3-CH₃ | H | CH₂CH₃ | CH₃ |
| A-52 | H | 3-CH₃ | 5-CH₃ | CH₂CH₃ | CH₃ |
| A-53 | H | 3-CH₃ | 5-Cl | CH₂CH₃ | CH₃ |
| A-54 | H | 3-CH₃ | 5-F | CH₂CH₃ | CH₃ |
| A-55 | H | 3-CH₃ | 5-CF₃ | CH₂CH₃ | CH₃ |
| A-56 | H | 3-CH₃ | H | CF₃ | CH₃ |
| A-57 | H | 3-CH₃ | 5-CH₃ | CF₃ | CH₃ |
| A-58 | H | 3-CH₃ | 5-Cl | CF₃ | CH₃ |
| A-59 | H | 3-CH₃ | 5-F | CF₃ | CH₃ |
| A-60 | H | 3-CH₃ | 5-CF₃ | CF₃ | CH₃ |
| A-61 | H | 2-CH₃ | H | CH₃ | CH₂CH₃ |
| A-62 | H | 2-CH₃ | 5-CH₃ | CH₃ | CH₂CH₃ |
| A-63 | H | 2-CH₃ | 5-Cl | CH₃ | CH₂CH₃ |
| A-64 | H | 2-CH₃ | 5-F | CH₃ | CH₂CH₃ |
| A-65 | H | 2-CH₃ | 5-CF₃ | CH₃ | CH₂CH₃ |
| A-66 | 6-CH₃ | 2-CH₃ | H | CH₃ | CH₂CH₃ |
| A-67 | 6-CH₃ | 2-CH₃ | 5-CH₃ | CH₃ | CH₂CH₃ |
| A-68 | 6-CH₃ | 2-CH₃ | 5-Cl | CH₃ | CH₂CH₃ |
| A-69 | 6-CH₃ | 2-CH₃ | 5-F | CH₃ | CH₂CH₃ |
| A-70 | 6-CH₃ | 2-CH₃ | 5-CF₃ | CH₃ | CH₂CH₃ |
| A-71 | 6-Cl | 2-CH₃ | H | CH₃ | CH₂CH₃ |
| A-72 | 6-Cl | 2-CH₃ | 5-CH₃ | CH₃ | CH₂CH₃ |
| A-73 | 6-Cl | 2-CH₃ | 5-Cl | CH₃ | CH₂CH₃ |
| A-74 | 6-Cl | 2-CH₃ | 5-F | CH₃ | CH₂CH₃ |
| A-75 | 6-Cl | 2-CH₃ | 5-CF₃ | CH₃ | CH₂CH₃ |
| A-76 | H | 2-CH₃ | H | CH₂CH₃ | CH₂CH₃ |
| A-77 | H | 2-CH₃ | 5-CH₃ | CH₂CH₃ | CH₂CH₃ |
| A-78 | H | 2-CH₃ | 5-Cl | CH₂CH₃ | CH₂CH₃ |
| A-79 | H | 2-CH₃ | 5-F | CH₂CH₃ | CH₂CH₃ |
| A-80 | H | 2-CH₃ | 5-CF₃ | CH₂CH₃ | CH₂CH₃ |
| A-81 | 6-CH₃ | 2-CH₃ | H | CH₂CH₃ | CH₂CH₃ |
| A-82 | 6-CH₃ | 2-CH₃ | 5-CH₃ | CH₂CH₃ | CH₂CH₃ |
| A-83 | 6-CH₃ | 2-CH₃ | 5-Cl | CH₂CH₃ | CH₂CH₃ |
| A-84 | 6-CH₃ | 2-CH₃ | 5-F | CH₂CH₃ | CH₂CH₃ |
| A-85 | 6-CH₃ | 2-CH₃ | 5-CF₃ | CH₂CH₃ | CH₂CH₃ |
| A-86 | 6-Cl | 2-CH₃ | H | CH₂CH₃ | CH₂CH₃ |
| A-87 | 6-Cl | 2-CH₃ | 5-CH₃ | CH₂CH₃ | CH₂CH₃ |
| A-88 | 6-Cl | 2-CH₃ | 5-Cl | CH₂CH₃ | CH₂CH₃ |
| A-89 | 6-Cl | 2-CH₃ | 5-F | CH₂CH₃ | CH₂CH₃ |

TABLE A-continued

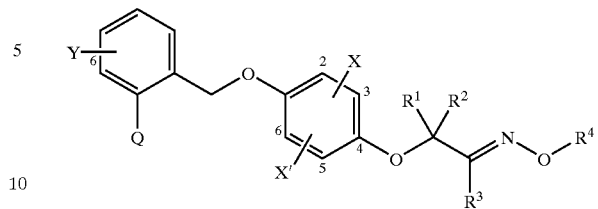

| No. | Y | X | X' | R³ | R⁴ |
|---|---|---|---|---|---|
| A-90 | 6-Cl | 2-CH₃ | 5-CF₃ | CH₂CH₃ | CH₂CH₃ |
| A-91 | H | 2-CH₃ | H | CF₃ | CH₂CH₃ |
| A-92 | H | 2-CH₃ | 5-CH₃ | CF₃ | CH₂CH₃ |
| A-93 | H | 2-CH₃ | 5-Cl | CF₃ | CH₂CH₃ |
| A-94 | H | 2-CH₃ | 5-F | CF₃ | CH₂CH₃ |
| A-95 | H | 2-CH₃ | 5-CF₃ | CF₃ | CH₂CH₃ |
| A-96 | 6-CH₃ | 2-CH₃ | H | CF₃ | CH₂CH₃ |
| A-97 | 6-CH₃ | 2-CH₃ | 5-CH₃ | CF₃ | CH₂CH₃ |
| A-98 | 6-CH₃ | 2-CH₃ | 5-Cl | CF₃ | CH₂CH₃ |
| A-99 | 6-CH₃ | 2-CH₃ | 5-F | CF₃ | CH₂CH₃ |
| A-100 | 6-CH₃ | 2-CH₃ | 5-CF₃ | CF₃ | CH₂CH₃ |
| A-101 | 6-Cl | 2-CH₃ | H | CF₃ | CH₂CH₃ |
| A-102 | 6-Cl | 2-CH₃ | 5-CH₃ | CF₃ | CH₂CH₃ |
| A-103 | 6-Cl | 2-CH₃ | 5-Cl | CF₃ | CH₂CH₃ |
| A-104 | 6-Cl | 2-CH₃ | 5-F | CF₃ | CH₂CH₃ |
| A-105 | 6-Cl | 2-CH₃ | 5-CF₃ | CF₃ | CH₂CH₃ |
| A-106 | H | 2-CH₃ | H | CH₃ | CH₂CH=CH₂ |
| A-107 | H | 2-CH₃ | 5-CH₃ | CH₃ | CH₂CH=CH₂ |
| A-108 | H | 2-CH₃ | 5-Cl | CH₃ | CH₂CH=CH₂ |
| A-109 | H | 2-CH₃ | 5-F | CH₃ | CH₂CH=CH₂ |
| A-110 | H | 2-CH₃ | 5-CF₃ | CH₃ | CH₂CH=CH₂ |
| A-111 | 6-CH₃ | 2-CH₃ | H | CH₃ | CH₂CH=CH₂ |
| A-112 | 6-CH₃ | 2-CH₃ | 5-CH₃ | CH₃ | CH₂CH=CH₂ |
| A-113 | 6-CH₃ | 2-CH₃ | 5-Cl | CH₃ | CH₂CH=CH₂ |
| A-114 | 6-CH₃ | 2-CH₃ | 5-F | CH₃ | CH₂CH=CH₂ |
| A-115 | 6-CH₃ | 2-CH₃ | 5-CF₃ | CH₃ | CH₂CH=CH₂ |
| A-116 | 6-Cl | 2-CH₃ | H | CH₃ | CH₂CH=CH₂ |
| A-117 | 6-Cl | 2-CH₃ | 5-CH₃ | CH₃ | CH₂CH=CH₂ |
| A-118 | 6-Cl | 2-CH₃ | 5-Cl | CH₃ | CH₂CH=CH₂ |
| A-119 | 6-Cl | 2-CH₃ | 5-F | CH₃ | CH₂CH=CH₂ |
| A-120 | 6-Cl | 2-CH₃ | 5-CF₃ | CH₃ | CH₂CH=CH₂ |
| A-121 | H | 2-CH₃ | H | CH₂CH₃ | CH₂CH=CH₂ |
| A-122 | H | 2-CH₃ | 5-CH₃ | CH₂CH₃ | CH₂CH=CH₂ |
| A-123 | H | 2-CH₃ | 5-Cl | CH₂CH₃ | CH₂CH=CH₂ |
| A-124 | H | 2-CH₃ | 5-F | CH₂CH₃ | CH₂CH=CH₂ |
| A-125 | H | 2-CH₃ | 5-CF₃ | CH₂CH₃ | CH₂CH=CH₂ |
| A-126 | 6-CH₃ | 2-CH₃ | H | CH₂CH₃ | CH₂CH=CH₂ |
| A-127 | 6-CH₃ | 2-CH₃ | 5-CH₃ | CH₂CH₃ | CH₂CH=CH₂ |
| A-128 | 6-CH₃ | 2-CH₃ | 5-Cl | CH₂CH₃ | CH₂CH=CH₂ |
| A-129 | 6-CH₃ | 2-CH₃ | 5-F | CH₂CH₃ | CH₂CH=CH₂ |
| A-130 | 6-CH₃ | 2-CH₃ | 5-CF₃ | CH₂CH₃ | CH₂CH=CH₂ |
| A-131 | 6-Cl | 2-CH₃ | H | CH₂CH₃ | CH₂CH=CH₂ |
| A-132 | 6-Cl | 2-CH₃ | 5-CH₃ | CH₂CH₃ | CH₂CH=CH₂ |
| A-133 | 6-Cl | 2-CH₃ | 5-Cl | CH₂CH₃ | CH₂CH=CH₂ |
| A-134 | 6-Cl | 2-CH₃ | 5-F | CH₂CH₃ | CH₂CH=CH₂ |
| A-135 | 6-Cl | 2-CH₃ | 5-CF₃ | CH₂CH₃ | CH₂CH=CH₂ |
| A-136 | H | 2-CH₃ | H | CF₃ | CH₂CH=CH₂ |
| A-137 | H | 2-CH₃ | 5-CH₃ | CF₃ | CH₂CH=CH₂ |
| A-138 | H | 2-CH₃ | 5-Cl | CF₃ | CH₂CH=CH₂ |
| A-139 | H | 2-CH₃ | 5-F | CF₃ | CH₂CH=CH₂ |
| A-140 | H | 2-CH₃ | 5-CF₃ | CF₃ | CH₂CH=CH₂ |
| A-141 | 6-CH₃ | 2-CH₃ | H | CF₃ | CH₂CH=CH₂ |
| A-142 | 6-CH₃ | 2-CH₃ | 5-CH₃ | CF₃ | CH₂CH=CH₂ |
| A-143 | 6-CH₃ | 2-CH₃ | 5-Cl | CF₃ | CH₂CH=CH₂ |
| A-144 | 6-CH₃ | 2-CH₃ | 5-F | CF₃ | CH₂CH=CH₂ |
| A-145 | 6-CH₃ | 2-CH₃ | 5-CF₃ | CF₃ | CH₂CH=CH₂ |
| A-146 | 6-Cl | 2-CH₃ | H | CF₃ | CH₂CH=CH₂ |
| A-147 | 6-Cl | 2-CH₃ | 5-CH₃ | CF₃ | CH₂CH=CH₂ |
| A-148 | 6-Cl | 2-CH₃ | 5-Cl | CF₃ | CH₂CH=CH₂ |
| A-149 | 6-Cl | 2-CH₃ | 5-F | CF₃ | CH₂CH=CH₂ |
| A-150 | 6-Cl | 2-CH₃ | 5-CF₃ | CF₃ | CH₂CH=CH₂ |
| A-151 | H | 2-CH₃ | H | CH₃ | CH₂C≡CH |
| A-152 | H | 2-CH₃ | 5-CH₃ | CH₃ | CH₂C≡CH |
| A-153 | H | 2-CH₃ | 5-Cl | CH₃ | CH₂C≡CH |
| A-154 | H | 2-CH₃ | 5-F | CH₃ | CH₂C≡CH |
| A-155 | H | 2-CH₃ | 5-CF₃ | CH₃ | CH₂C≡CH |

TABLE A-continued

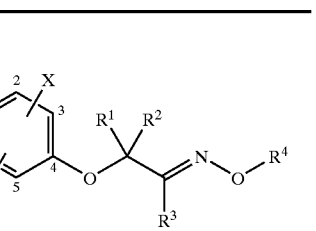

| No. | Y | X | X' | R³ | R⁴ |
|---|---|---|---|---|---|
| A-156 | 6-CH₃ | 2-CH₃ | H | CH₃ | CH₂C≡CH |
| A-157 | 6-CH₃ | 2-CH₃ | 5-CH₃ | CH₃ | CH₂C≡CH |
| A-158 | 6-CH₃ | 2-CH₃ | 5-Cl | CH₃ | CH₂C≡CH |
| A-159 | 6-CH₃ | 2-CH₃ | 5-F | CH₃ | CH₂C≡CH |
| A-160 | 6-CH₃ | 2-CH₃ | 5-CF₃ | CH₃ | CH₂C≡CH |
| A-161 | 6-Cl | 2-CH₃ | H | CH₃ | CH₂C≡CH |
| A-162 | 6-Cl | 2-CH₃ | 5-CH₃ | CH₃ | CH₂C≡CH |
| A-163 | 6-Cl | 2-CH₃ | 5-Cl | CH₃ | CH₂C≡CH |
| A-164 | 6-Cl | 2-CH₃ | 5-F | CH₃ | CH₂C≡CH |
| A-165 | 6-Cl | 2-CH₃ | 5-CF₃ | CH₃ | CH₂C≡CH |
| A-166 | H | 2-CH₃ | H | CH₂CH₃ | CH₂C≡CH |
| A-167 | H | 2-CH₃ | 5-CH₃ | CH₂CH₃ | CH₂C≡CH |
| A-168 | H | 2-CH₃ | 5-Cl | CH₂CH₃ | CH₂C≡CH |
| A-169 | H | 2-CH₃ | 5-F | CH₂CH₃ | CH₂C≡CH |
| A-170 | H | 2-CH₃ | 5-CF₃ | CH₂CH₃ | CH₂C≡CH |
| A-171 | 6-CH₃ | 2-CH₃ | H | CH₂CH₃ | CH₂C≡CH |
| A-172 | 6-CH₃ | 2-CH₃ | 5-CH₃ | CH₂CH₃ | CH₂C≡CH |
| A-173 | 6-CH₃ | 2-CH₃ | 5-Cl | CH₂CH₃ | CH₂C≡CH |
| A-174 | 6-CH₃ | 2-CH₃ | 5-F | CH₂CH₃ | CH₂C≡CH |
| A-175 | 6-CH₃ | 2-CH₃ | 5-CF₃ | CH₂CH₃ | CH₂C≡CH |
| A-176 | 6-Cl | 2-CH₃ | H | CH₂CH₃ | CH₂C≡CH |
| A-177 | 6-Cl | 2-CH₃ | 5-CH₃ | CH₂CH₃ | CH₂C≡CH |
| A-178 | 6-Cl | 2-CH₃ | 5-Cl | CH₂CH₃ | CH₂C≡CH |
| A-179 | 6-Cl | 2-CH₃ | 5-F | CH₂CH₃ | CH₂C≡CH |
| A-180 | 6-Cl | 2-CH₃ | 5-CF₃ | CH₂CH₃ | CH₂C≡CH |
| A-181 | H | 2-CH₃ | H | CF₃ | CH₂C≡CH |
| A-182 | H | 2-CH₃ | 5-CH₃ | CF₃ | CH₂C≡CH |
| A-183 | H | 2-CH₃ | 5-Cl | CF₃ | CH₂C≡CH |
| A-184 | H | 2-CH₃ | 5-F | CF₃ | CH₂C≡CH |
| A-185 | H | 2-CH₃ | 5-CF₃ | CF₃ | CH₂C≡CH |
| A-186 | 6-CH₃ | 2-CH₃ | H | CF₃ | CH₂C≡CH |
| A-187 | 6-CH₃ | 2-CH₃ | 5-CH₃ | CF₃ | CH₂C≡CH |
| A-188 | 6-CH₃ | 2-CH₃ | 5-Cl | CF₃ | CH₂C≡CH |
| A-189 | 6-CH₃ | 2-CH₃ | 5-F | CF₃ | CH₂C≡CH |
| A-190 | 6-CH₃ | 2-CH₃ | 5-CF₃ | CF₃ | CH₂C≡CH |
| A-191 | 6-Cl | 2-CH₃ | H | CF₃ | CH₂C≡CH |
| A-192 | 6-Cl | 2-CH₃ | 5-CH₃ | CF₃ | CH₂C≡CH |
| A-193 | 6-Cl | 2-CH₃ | 5-Cl | CF₃ | CH₂C≡CH |
| A-194 | 6-Cl | 2-CH₃ | 5-F | CF₃ | CH₂C≡CH |
| A-195 | 6-Cl | 2-CH₃ | 5-CF₃ | CF₃ | CH₂C≡CH |

The compounds I are suitable for use as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
*Botrytis cinerea* (gray mold) on strawberries, vegetables, ornamentals and grapevines,
*Cercospora arachidicola* on peanuts,
*Erysiphe cichoracearum* and *Sphaerotheca fuliginea* on cucurbits,
*Erysiphe graminis* (powdery mildew) on cereals,
Fusarium and Verticillium species on various plants,
Helminthosporium species on cereals,
Mycosphaerella species on bananas and peanuts,
*Phytophthora infestans* on potatoes and tomatoes,
*Plasmopara viticola* on grapevines,
*Podosphaera leucotricha* on apples,
*Pseudocercosporella herpotrichoides* on wheat and barley,
Pseudoperonospora species on hops and cucumbers,
Puccinia species on cereals,
*Pyricularia oryzae* on rice,
Rhizoctonia species on cotton, rice and lawns,
*Septoria nodorum* on wheat,
*Uncinula necator* on grapevines,
Ustilago species on cereals and sugar cane, and
Venturia species (scab) on apples and pears.

Moreover, the compounds I are suitable for controlling harmful fungi such as *Paecilomyces variotii* in the protection of materials (e.g. wood, paper, paint dispersions, fibers and fabrics) and in the protection of stored products.

The compounds I are applied by treating the fungi, or the plants, seeds, materials or the soil to be protected against fungal attack, with a fungicidally effective amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; in any case, it should ensure a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol or formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading or granules, by means of spraying, atomizing, dusting, spreading or pouring. The use forms depend entirely on the intended purposes; in any case, they are intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such, or dissolved in an oil or solvent, can be homogenized in water by means of a wetting agent, tackifier, dispersant or emulsifier. Alternatively, it is possible to prepare concentrates composed of an active substance, wetting agent, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides or bactericides may be added to the active ingredients, if appropriate also only immediately prior to use (tank mix). These agents can be admixed with the compositions according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)phosphinyl]-3-phenyl-1,2,4-triazole, 2,3-dicyano-1,4-dithioanthraquinone, 2-thio-1,3-dithiolo-[4,5-b] quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 8-(1,1-dimethylethyl)-N-ethyl-N-propyl-1,4-dioxaspiro[4.5] decane-2-methanamine;

azoles such as 1-[2-(2,4-dichlorophenyl)-4-ethyl-1,3-5 dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, 1-[2-(2,4-dichlorophenyl)pentyl]-1H-1,2,4-triazole, 2,4'-difluoro-α-1H-1,2,4-triazolyl-1-methyl)benzhydryl alcohol, 1-((bis-(4-fluorophenyl) methylsilyl)methyl)-1H-1,2,4-triazole, 1-[(2RS,4RS; 2RS, 4SR)-4-bromo-2-(2,4-dichlorophenyl) tetrahydrofuryl]-1H-1,2,4-triazole, 2-(4-chlorophenyl)-3-cyclopropyl-1-1H-1,2,4-triazol-1-yl)-butan-2-ol, (+)-4-chloro-4-[4-methyl-2-1H-1,2,4-triazol-1-ylmethyl)-1,3-dioxolan-2-yl]phenyl 4-chlorophenyl ether, (E)-(R, S)-1-(2,4-dichlorophenyl)-4,4-dimethyl-2-1H-1,2,4-triazol-1-yl)pent-1-en-3-ol, 4-(4-chlorophenyl)-2-phenyl-2-1H-1,2,4-triazolylmethyl)butyronitrile, 3-(2,4-dichlorophenyl)-6-fluoro-2-1H-1,2,4-triazol-1-yl)-quinazolin-4(3H)-one, (R,S)-(2-(2,4-dichlorophenyl)-1H-1,2,4-triazol-1-yl)hexan-2-ol, (1RS, 5RS; 1RS, 5SR)-5-(4-chlorobenzyl)-2,2-dimethyl-1-1H-1,2,4-triazol-1-yl-methyl)-cyclopentanol, (R,S)-1-(4-chlorophenyl)-4,4-dimethyl-3-1H-1,2,4-triazol-1-ylmethyl)pentan-3-ol, (+)-2-(2,4-30 dichlorophenyl)-3-1H-1,2,4-triazolyl)propyl 1,1,2,2-tetrafluoroethyl ether, (E)-{1-[1-(4-chloro-2-trifluoromethyl)phenyl] imino-2-propoxyethyl}-1H-imidazole, 2-(4-chlorophenyl)-2-1H-1,2,4-triazol-1-ylmethyl) hexanenitrile;

α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurines such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]acetamide, methyl E-methoxyimino [α-(2,5-dimethylphenoxy)-o-tolyl]acetamide, methyl E-2-{2-[(2-trifluoromethylpyridyl-6-oxymethyl) phenyl}-3-methoxyacrylate, methyl (E,E)-methoximino-{2-[1-(3-tri-fluoromethylphenyl) ethylideneaminooxymethyl]phenyl}acetate;

methyl N-(2-{[1-(4-chlorophenyl)-1H-pyrazol-3-yl] oxymethyl}phenyl)-N-methoxycarbamate;

anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline;

phenylpyrroles such as 4-(2,2-difluoro-1,3-benzodioxol-4-yl)-pyrrole-3-carbonitrile;

cinnamamides such as 3-(4-chlorophenyl)-3-(3,4-dimethoxyphenyl)acryloylmorpholide;

and a variety of fungicides such as dodecylguanidine acetate, 3-[3-(3,5-dimethyl-2-oxycyclohexyl)-2-hydroxyethyl]glutarimide, N-methyl-N-ethyl-(4-trifluoromethyl)-2-[3', 4'-dimethoxyphenyl]benzamide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethyl-phenyl)-N-chloroacetyl-D,L-2-amino butyrolactone, DL-N-(2,6-dimethylphenyl)-N-(phenylacetyl) alanine methyl ester, 5-methyl-5-vinyl-3-(3,5-dichlorophenyl)-2,4-dioxo-1,3-oxa- zolidine, 3-(3,5-dichlorophenyl)-5-methyl-5-methoxymethyl-1,3-oxazolidine-2,4-dione, 3-(3,5-dichlorophenyl)-1-isopropyl- carbamoylhydantoin, N-(3,5-dichlorophenyl)-1,2-dimethyl-cyclopropane-1,2-dicarboximide, 2-cyano-[N-(ethylaminocarbonyl)-2-methoximino]acetamide, N-(3-chloro-2,6-dinitro-4-trifluoromethylphenyl)-5-trifluoromethyl-3-chloro-2-aminopyridine.

SYNTHESIS EXAMPLES

With due modification of the starting compounds, the protocols shown in the synthesis examples below were used for obtaining further compounds I. The resulting compounds, together with physical data, are listed in the Table which follows.

Example 1

Preparation of Methyl [2-(4-Acetoxy-2-methylphenoxymethyl)phenyl]methoxyimino Acetate

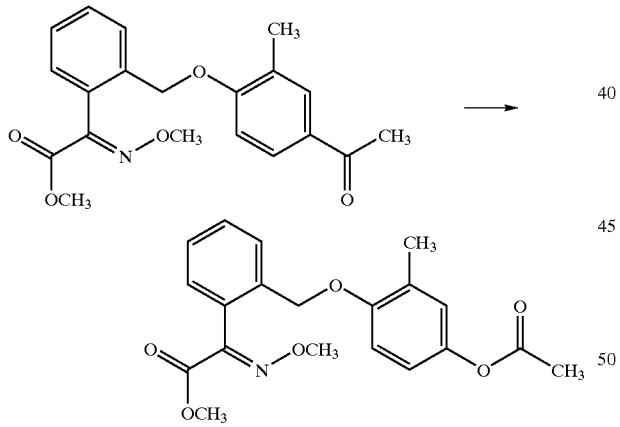

A solution of 106.1 g of methyl E-2-[(2'-methyl-41-acetyl)phenoxymethyl]phenylglyoxylate O-methyl oxime [cf. EP-A 621 264] in 240 ml of CH$_2$Cl$_2$ was admixed with 188.3 g of 3-chloroperbenzoic acid (MCPBA) and then stirred at 20–25° C. for about 3 days. The precipitate was filtered off and the organic phases were washed with sat. solutions of NaS$_2$O$_3$ and NaHCO$_3$ and water, and the solvent was then distilled off. The residue gave 104 g of the title compound as a light-brown crystalline substance of m.p. 108–1100C.

$^1$H-NMR (δ [CDCl$_3$]): 2.2 (s, 3H); 2.3 (s, 3H); 3.8 (s, 3H); 4.0 (s, 3H); 5.0 (s, 3H); 6.7–7.0 (m, 3H); 7.2–7.6 (m, 4H).

Example 2

Preparation of Methyl [2-(4-Hydroxy-2-methylphenoxymethyl)phenyl]methoxyimino Acetate

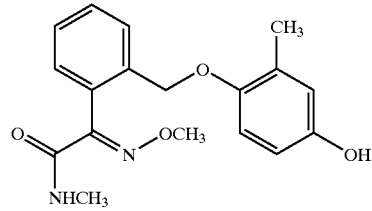

A solution of 50.7 g of the compound from Example 1 in 80 ml of tetrahydrofuran (THF) was admixed with 42 g of 40% strength aqueous methylamine solution and then stirred at 20–25° C. for about 12 h. The solvent was distilled off and the residue was taken up in a mixture of methyl tert-butyl ether/water, and the phases were then separated. After drying, the solvent was removed from the organic phase. The residue gave, after digestion with diisopropyl ether, 40.6 g of the title compound as a light-brown crystalline substance of m.p. 148–150° C.

$^1$H-NMR (δ [CDCl$_3$]): 2.2 (s, 3H); 3.0 (d, 3H); 4.0 (s, 3H); 5.0 (s, 2H); 4.6 (s, 1H); 6.6 (m, 1H); 6.7–7.6 (m, 7H).

Example 3

Preparation of 2-Methoxyimino-N-methyl-2-{2-[2-methyl-4-(1-methyl-2-oxopropoxy)phenoxymethyl]phenyl}acetamide

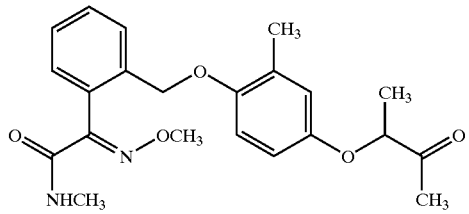

A solution of 22 g of the compound from Example 2 in 200 ml of dimethylformamide (DMF) was admixed with 50 g of K$_2$CO$_3$ and 8.5 g of 3-chloro-2-butanone and then stirred at about 50° C. for 5 h. The solvent was distilled off and the residue was taken up in a mixture of methyl tert-butyl ethyl/water, and the phases were then separated. After drying, the solvent was removed from the organic phase. The residue gave 21.7 g of the title compound as a brown oil.

$^1$H-NMR (δ [CDCl$_3$]): 1.4 (d, 3H); 1.18 (s, 3H); 1.2 (s, 3H); 3.0 (d, 3H); 4.0 (3H); 4.5 (q, 1H); 5.0 (s, 2H).

Example 4

Preparation of 2-Methoxyimino-2-{2-[4-(2-methoxyimino-1-methyl-propoxy)-2-methylphenoxymethyl]phenyl}-N-methyl-acetamide [I-1]

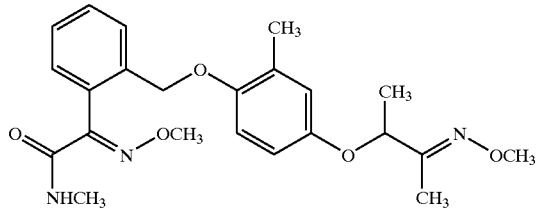

A solution of 21.7 g of the compound from Example 3 in 100 ml of methanol was admixed with 30.4 g of 30% strength aqueous methoxyamine solution and then stirred at 20–25° C. for 12 h. The solvent was distilled off and the residue was taken up in a mixture of methyl tert-butyl ether/water, and the phases were then separated. After drying, the solvent was removed from the organic phase. The residue gave 22 g of the title compound as a light-brown oil.

$^1$H-NMR (δ [CDCl$_3$]): 1.4 (d, 3H); 1.8 (s, 3H); 2.8 (d, 3H); 3.8 (s, 3H); 4.0 (s, 3H); 4.8 (q, 1H); 5.0 (s, 2H).

Example 5

Preparation of Methyl [2-(4-Hydroxy-2-methylphenoxymethyl)phenyl]methoxyimino Acetate

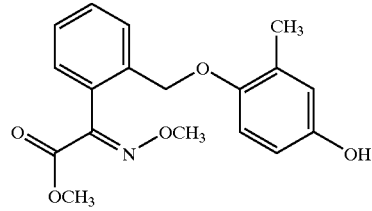

A solution of 50.7 g of the compound from Example 1 in 15 ml of 30% strength methanolic sodium methoxide solution was refluxed for 2 h. The solvent was distilled off and the residue was taken up in a mixture of CH$_2$Cl$_2$/NH$_4$Cl solution, and the phases were then separated. After washing with NH$_4$Cl solution and drying, the solvent was removed from the organic phase. The residue gave 39.2 g of the title compound as a light-brown crystalline substance of m.p. 143–146° C.

$^1$H-NMR (δ [CDCl$_3$]): 2.2 (s, 3H); 3.8 (s, 3H); 4.0 (s, 3H); 4.6 (s, 1H[OH]); 4.9 (s, 2H).

TABLE I

| No. | Q | Y | X | X' | R$^1$ | R$^2$ | R$^3$ | R$^4$ | Physical data $^1$H-NMR (δ [ppm]) |
|---|---|---|---|---|---|---|---|---|---|
| I-1 | C(=NOCH$_3$)—CONHCH$_3$ | H | 2-CH$_3$ | H | CH$_3$ | H | CH$_3$ | CH$_3$ | (see Example 4) |
| I-2 | C(=NOCH$_3$)—CONHCH$_3$ | H | 2-CH$_3$ | H | CH$_3$ | H | CH$_3$ | CH$_2$CH$_3$ | 1.2(t); 1.4(d); 1.8(s); 2.2(s); 2.8(d); 3.9(s); 4.1(m); 4.8(m); 4.9(s) |
| I-3 | C(=NOCH$_3$)—CONHCH$_3$ | H | 2-CH$_3$ | H | CH$_3$ | H | CH$_3$ | CH$_2$—CH=CH$_2$ | 1.4(d); 1.8(s); 2.2(s); 2.8(d); 3.9(s); 4.6(t); 4.8(m); 4.9(s); 5.2(m); 6.0(m) |
| I-4 | C(=NOCH$_3$)—CONHCH$_3$ | H | 2-CH$_3$ | H | CH$_3$ | H | CH$_3$ | CH$_2$CH$_2$CH$_3$ | 0.8(m); 1.4(d); 1.8(s); 2.2(d); 2.9(d); 3.9(s); 4.0(m); 4.8(m); 4.9(s) |
| I-5 | C(=NOCH$_3$)—CONHCH$_3$ | H | 2-CH$_3$ | H | CH$_3$ | H | CH$_3$ | CH(CH$_3$)$_2$ | 1.2(m); 1.4(d); 1.7(s); 2.2(s); 2.8(d); 3.9(s); 4.3(m); 4.8(m); 4.9(s) |
| I-6 | C(=NOCH$_3$)—CONHCH$_3$ | H | 2-CH$_3$ | H | CH$_3$ | H | CH$_3$ | CH$_2$—C≡CH | 1.4(d); 1.8(s); 2.8(d); 3.9(s); 4.6(d); 4.9(s) |
| I-7 | C(=NOCH$_3$)—CONHCH$_3$ | H | 2-CH$_3$ | H | CH$_3$ | H | CH$_3$ | (Z) CH$_2$—CH=CHCl | 1.4(d); 1.8(s); 2.2(s); 2.9(d); 3.9(s); 4.8(m); 4.9(s); 6.0(m) |
| I-8 | C(=NOCH$_3$)—CONHCH$_3$ | H | 2-CH$_3$ | H | CH$_3$ | H | CH$_3$ | (E) CH$_2$—CH=CHCl | 1.4(d); 1.8(s); 2.2(s); 2.8(d); 3.9(s); 4.5(d); 4.8(m); 6.1(m) |
| I-9 | C(=NOCH$_3$)—CONHCH$_3$ | H | 2-CH$_3$ | H | CH$_3$ | H | CH$_3$ | CH(CH$_3$)C≡CH | 1.5(d); 1.8(s); 2.2(s); 2.8(d); 3.9(s); 4.8(d) |
| I-10 | C(=NOCH$_3$)—CONHCH$_3$ | H | 2-CH$_3$ | H | CH$_3$ | H | CH$_3$ | CH$_2$CCl=CH$_2$ | 1.4(d); 1.8(s); 2.2(s); 2.8(d); 3.9(s); 4.6(s); 4.8(m); 4.9(s) |

EXAMPLES FOR THE ACTION AGAINST HARMFUL FUNGI

The fungicidal action of the compounds of the formula I was demonstrated by the following experiments:

The active ingredients were formulated as a 10% strength emulsion in a mixture of 63% by weight of cyclohexanone and 27% by weight of emulsifier and diluted to the desired concentration with water.

The compound A, known from EP-A 477 631 as No. 415, and the compound B, known from EP-A 579 124 as No. I.007, served as comparative active ingredients:

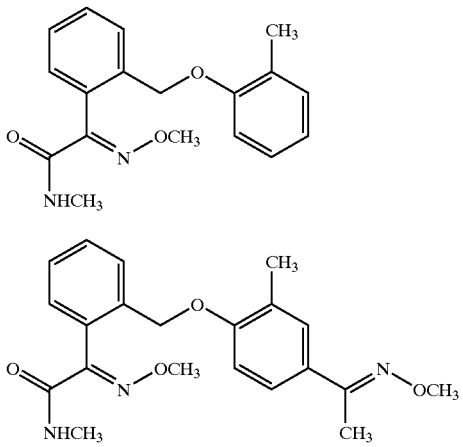

Use Example 1

Activity Against Powdery Mildew of Wheat

Leaves of potted wheat seedlings c.v. "Frühgold" were sprayed to run off point with an aqueous preparation of active ingredient which had been prepared using a stock solution of 10% of active ingredient, 63% of cyclohexanone and 27% of emulsifier and, 24 hours after the spray coating had dried on, dusted with spores of powdery mildew of wheat (*Erysiphe graminis forma specialis tritici*). The test plants were subsequently placed in a greenhouse at 20–24° C. and 60–90% relative atmospheric humidity. After 7 days, the extent of the mildew development was scored visually in % infection of the total leaf area.

In this test, the plants which had been treated with 1 ppm of the active ingredient I-1 of Table I showed no infection, whereas the plants which had been treated with 1 ppm of the comparative active ingredients A and B were infected to 60% and 25%, respectively, and the untreated plants were infected to 90%.

Use Example 2

Curative Activity Against *Puccinia Recondita* on Wheat (Leaf Rust of Wheat)

Leaves of potted wheat seedlings c.v. "Kanzler" were dusted with leaf rust spores (*Puccinia recondita*). The pots were then placed for 24 hours in a chamber with high atmospheric humidity (90 to 95%) at 20 to 22° C. During this time, the spores germinated, and the germinal tubes penetrated the leaf tissue. The next day, the infected plants were sprayed to run off point with an aqueous preparation of active ingredient which had been prepared using a stock solution of 10% of active ingredient, 63% of cyclohexanone and 27% of emulsifier. After the spray coating had dried on, the test plants were cultivated for 7 days in a greenhouse at 20–22° C. and a relative atmospheric humidity of 65–70%. The extent of rust development on the leaves was then determined.

In this test, the plants which had been treated with 16 ppm of the active ingredients I-1 to I-10 of Table I showed no infection, whereas the plants which had been treated with 16 ppm of the comparative active ingredients A and B were infected to 60% and 25%, respectively, and the untreated plants were infected to 95%.

Use Example 3—Activity against *Pyricularia oryzae* (protective)

Leaves of potted rice seedlings c.v. "Tai-Nong 67" were sprayed to run off point with an aqueous preparation of active ingredient which had been prepared using a stock solution of 10% of active ingredient, 63% of cyclohexanone and 27% of emulsifier. The next day, the plants were inoculated with an aqueous spore suspension of *Pyricularia oryzae*. The test plants were subsequently placed into controlled-environment chambers at 22–24° C. and a relative atmospheric humidity of 95–99% for 6 days. The extent of the development of the infection on the leaves was then determined visually.

In this test, the plants which had been treated with 63 ppm of the active ingredients I-1 to I-10 of Table I showed no infection, whereas the plants which had been treated with 63 ppm of the comparative active ingredients A and B were infected to 25% and 40%, respectively, and the untreated plants were infected to 85%.

We claim:

1. An iminooxy-substituted benzyl phenyl ether compound of formula I

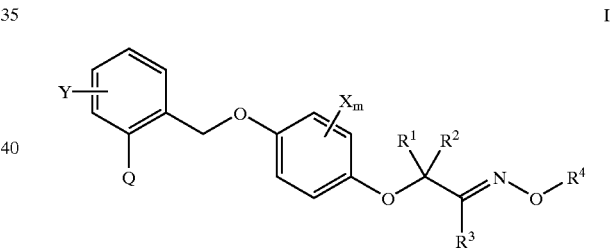

in which the substituents and the index have the following meanings:

Y is H, $CH_3$, F or Cl;

Q is $C(=CHOCH_3)—COOCH_3$, $C(=CHCH_3)—COOCH_3$, $C(=NOCH_3)—COOCH_3$, $C(=NOCH_3)—CONHCH_3$ or $N(—OCH_3)—COOCH_3$;

X is hydrogen, halogen, $C_1–C_4$-alkyl, $C_1–C_4$-alkoxy or $CF_3$;

m is 1 or 2, where the radicals X may be different if m=2;

$R^1$ is $C_1–C_4$-alkyl and $R^2$ is hydrogen or $C_1–C_4$-alkyl; or $R^1$ and $R^2$ together are cyclopropyl, cyclopentyl or cyclohexyl;

$R^3$ is $C_1–C_6$-alkyl or $CF_3$;

$R^4$ is $C_1–C_4$-alkyl, $C_3–C_4$-alkenyl, $C_3–C_4$-alkynyl, $C_1–C_4$-haloalkyl, $C_3–C_4$-haloalkenyl or $C_3–C_4$-haloalkynyl;

or a salt thereof.

2. The ether compound of formula I defined in claim 1 which is represented by formula I'

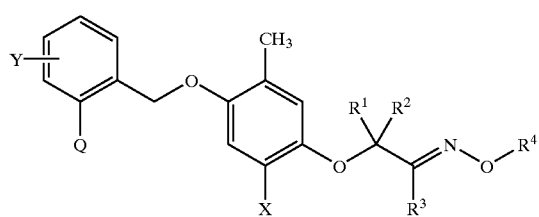

and in which X is hydrogen, methyl, chlorine or fluorine.

3. The ether compound of formula I' defined in claim 2 in which Y is located in the 6-position, X is hydrogen and $R^1$ is methyl, ethyl, isopropyl or cyclopropyl, $R^2$ is hydrogen and $R^3$ is methyl or ethyl.

4. The ether compound of formula I defined in claim 1 which is represented by formula I"

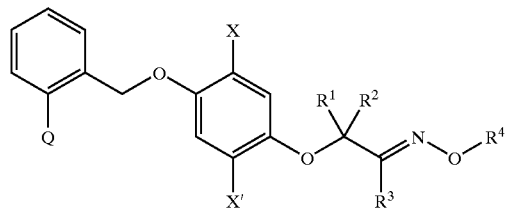

and wherein X' is a radical selected from the groups enumerated for X.

5. The ether compound of formula I" defined in claim 4 in which X and $R^1$ are methyl and X' and $R^2$ are hydrogen.

6. A process for preparing the ether compound of formula I defined in claim 1, which comprises oxidizing an acetyl compound of formula II.1

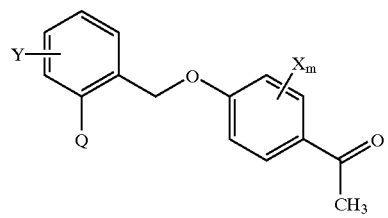

to obtain an O-acetyl compound of formula II.2

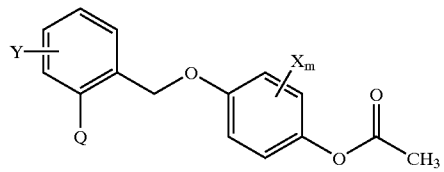

reacting the O-acyl compound under basic conditions to obtain a hydroxy compound of formula II,

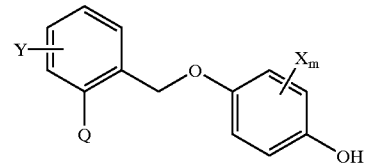

reacting the hydroxy compound with a keto compound of formula III

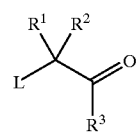

in which L is a nucleophilically exchangeable group, to obtain a compound of formula IV

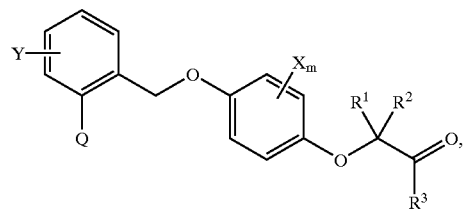

and oximating the compound of formula IV with an amino compound of formula V $$H_2N\text{—}OR^4 \qquad V$$

or a corresponding acid addition salt thereof to obtain the ether compound of formula I.

7. The process of claim 6 for preparing the ether compound of formula I in which Q is $C(=NOCH_3)$—$CONHCH_3$, wherein the acetyl compound is of formula II.1'

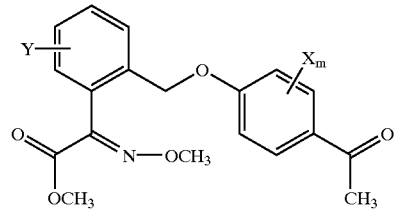

the O-acetyl compound is of formula II.2'

II.2' 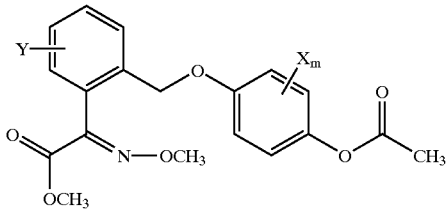

and the O-acetyl compound is reacted with methylamine to obtain the hydroxy compound of formula II in which Q is $C(=NOCH_3)-CONHCH_3$.

8. A composition suitable for controlling harmful fungi, comprising a solid or liquid carrier and the ether compound of formula I defined in claim 1.

9. A method for controlling harmful fungi, which comprises treating the fungi, or materials, plants, soil or seeds to be protected against fungal attack, with an effective amount of the ether compound of formula I defined in claim 1.

* * * * *